United States Patent
Watt et al.

(10) Patent No.: US 10,632,156 B2
(45) Date of Patent: Apr. 28, 2020

(54) PREPARATION OF SMALL COLONY VARIANTS OF THERAPEUTIC BACTERIA

(71) Applicant: ATTERX BIOTHERAPEUTICS, INC., Madison, WI (US)

(72) Inventors: Steven R. Watt, Windsor, WI (US); Caleb W. Dorsey, Verona, WI (US); Joshua A. Smith, New Glarus, WI (US)

(73) Assignee: Atterx Biotherapeutics, Inc., Madison, WI (US)

( * ) Notice: Subject to any disclaimer, the term of this patent is extended or adjusted under 35 U.S.C. 154(b) by 173 days.

(21) Appl. No.: 15/129,611

(22) PCT Filed: Mar. 27, 2015

(86) PCT No.: PCT/US2015/023026
§ 371 (c)(1),
(2) Date: Sep. 27, 2016

(87) PCT Pub. No.: WO2015/148943
PCT Pub. Date: Oct. 1, 2015

(65) Prior Publication Data
US 2017/0173087 A1    Jun. 22, 2017

Related U.S. Application Data

(60) Provisional application No. 61/971,913, filed on Mar. 28, 2014.

(51) Int. Cl.
*A61K 35/741*    (2015.01)
*C12N 1/20*    (2006.01)
(Continued)

(52) U.S. Cl.
CPC .......... *A61K 35/741* (2013.01); *A61K 9/0034* (2013.01); *A61K 35/74* (2013.01);
(Continued)

(58) Field of Classification Search
None
See application file for complete search history.

(56) References Cited

U.S. PATENT DOCUMENTS

| 4,597,966 A | 7/1986 | Zolton et al. |
| 5,536,645 A | 7/1996 | Jay |

(Continued)

FOREIGN PATENT DOCUMENTS

| WO | WO 2009/005704 | | 1/2009 |
| WO | WO 2009/020455 | * | 2/2009 |

OTHER PUBLICATIONS

Trautner et al., J. Urol. 167(1): 375-379 (2002).*
Lim et al., J. Microbiol. Biotechnol. 14(1): 90-96 (2004).*
Borderon et al., J. Clin. Microbiol. 8(6): 629-634 (1978).*
Lessard, Methods Enzymol. 533: 181-189 (2013).*
OpenWetWare, "Neidhardt EZ Rich Defined", https://openwetware.org/wiki/Neidhardt_EZ_Rich_Defined, 2008.*

(Continued)

*Primary Examiner* — Erin M. Bowers
(74) *Attorney, Agent, or Firm* — Casimir Jones, S.C.; Mary Ann D. Brow

(57) ABSTRACT

The invention relates to methods of differentiation, isolation, propagation, and storage of small colony variants (SCVs) of *E. coli*, preferably *E. coli* 83972 or *E. coli* HU2117, or modified or variant forms thereof, and methods for using the prepared SCV bacteria to establish probiotic biofilms in treated subjects and/or on treated medical devices.

15 Claims, 5 Drawing Sheets

Figure 1:
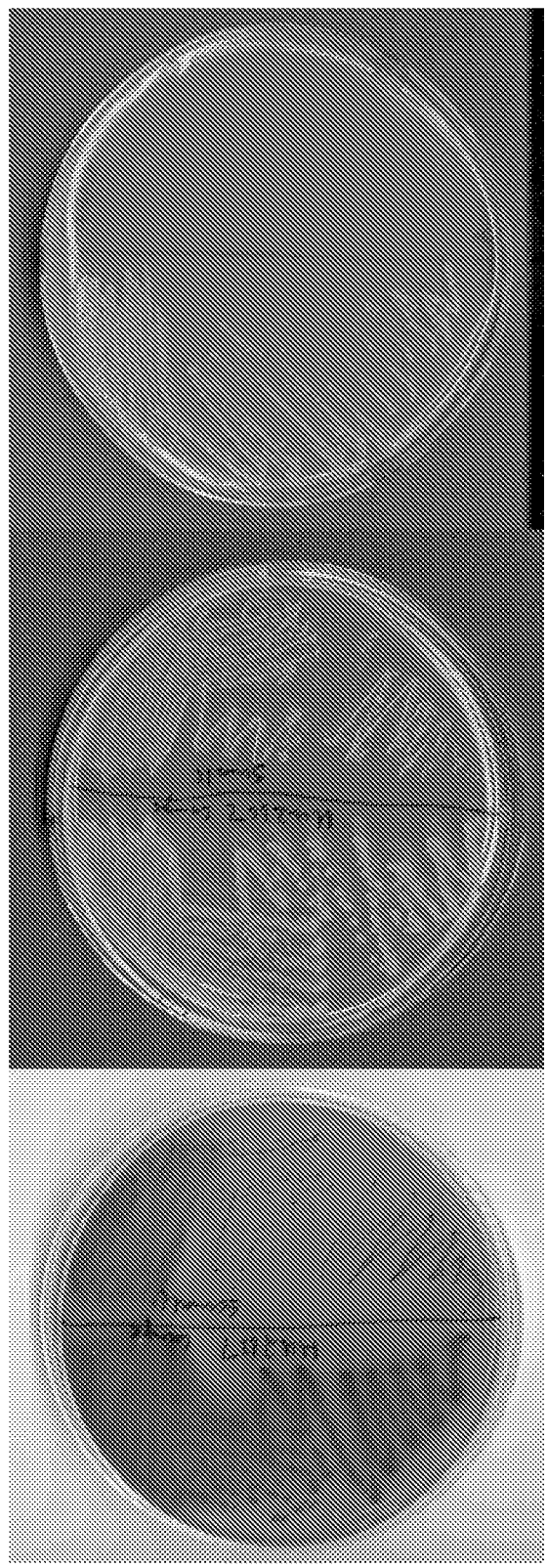

(51) Int. Cl.

| | | |
|---|---|---|
| *A61M 25/00* | (2006.01) | |
| *A61L 29/14* | (2006.01) | |
| *A61L 29/00* | (2006.01) | |
| *A61K 35/74* | (2015.01) | |
| *A61L 29/08* | (2006.01) | |
| *C12N 1/38* | (2006.01) | |
| *A61K 9/00* | (2006.01) | |
| *C12N 1/32* | (2006.01) | |

(52) U.S. Cl.
CPC .......... *A61L 29/005* (2013.01); *A61L 29/085* (2013.01); *A61L 29/145* (2013.01); *A61M 25/0045* (2013.01); *C12N 1/20* (2013.01); *C12N 1/32* (2013.01); *C12N 1/38* (2013.01); *A61L 2400/10* (2013.01); *A61M 25/0017* (2013.01); *A61M 2025/0046* (2013.01); *C12N 2500/05* (2013.01); *C12N 2500/14* (2013.01); *C12N 2500/16* (2013.01); *C12N 2500/20* (2013.01); *C12N 2500/22* (2013.01); *C12N 2500/24* (2013.01); *C12N 2500/32* (2013.01); *C12N 2500/34* (2013.01); *C12N 2500/60* (2013.01)

(56) References Cited

U.S. PATENT DOCUMENTS

| | | | |
|---|---|---|---|
| 8,715,639 | B2 | 5/2014 | Suzuki et al. |
| 2006/0035287 | A1 | 2/2006 | Kroll et al. |
| 2006/0270040 | A1 | 11/2006 | Filutowicz et al. |
| 2007/0118916 | A1 | 5/2007 | Puzio et al. |
| 2009/0041727 | A1 | 2/2009 | Suzuki et al. |
| 2010/0195823 | A1 | 8/2010 | Fukuoka et al. |
| 2010/0279331 | A1 | 11/2010 | Moriyama et al. |
| 2011/0287500 | A1 | 11/2011 | Urano et al. |
| 2012/0045432 | A9 | 2/2012 | Yu et al. |
| 2012/0115180 | A1 | 5/2012 | Lahteenmaki et al. |
| 2013/0029415 | A1 | 1/2013 | Naoya et al. |
| 2013/0122541 | A1 | 5/2013 | Lynch et al. |
| 2013/0195823 | A1* | 8/2013 | Scatizzi .............. A61K 35/747 424/93.45 |
| 2013/0211310 | A1 | 8/2013 | Bommarito et al. |
| 2013/0297680 | A1 | 10/2013 | Ovaa et al. |
| 2013/0302783 | A1 | 11/2013 | Hayashizaki et al. |
| 2013/0323808 | A1 | 12/2013 | Gokarn et al. |
| 2014/0051841 | A1 | 2/2014 | Allen et al. |
| 2015/0110759 | A1 | 4/2015 | Suzuki et al. |

OTHER PUBLICATIONS

Clowes et al., Genetic studies on small-colony variants of *Escherichia coli* K-12. J Gen Microbiol. Dec. 1955;13(3):461-73.

Vejborg et al., Identification of genes important for growth of asymptomatic bacteriuria *Escherichia coli* in urine. Infect Immun. Sep. 2012;80(9):3179-88.

Extended European Search Report for EP 15769474.6, dated Oct. 9, 2017, 8 pages.

Bouatra et al., The human urine metabolome. PLoS One. Sep. 4, 2013;8(9):e73076.

Brooks et al., A simple artificial urine for the growth of urinary pathogens. Lett Appl Microbiol. Mar. 1997;24(3):203-6.

Colwell, Small Colony Variants of z*Escherichia coli*. J Bacteriol. Oct. 1946;52(4):417-22.

Darouiche et al., Bacterial Interference for Prevention of Urinary Tract Infection. Clinical Infectious Diseases. 2012;55(10):1400-7.

Ferrieres et al., Biofilm exclusion of uropathogenic bacteria by selected asymptomatic bacteriuria *Escherichia coli* strains. Microbiology 2007;153:1711-19.

Hirsch, Small colony variants of *Escherichia coli*. Mode of action of copper in variant recovery and population dynamics of cultures containing variants. J Bacteriol. Mar. 1961;81:448-58.

Neidhardt et al., Culture medium for enterobacteria. J Bacteriol. Sep. 1974;119(3):736-47.

Nicolle, Catheter-related urinary tract infection. Drugs Aging. 2005;22(8):627-39.

Prasad et al., A Bacterial Interference Strategy for Prevention of UTI in Persons Practicing Intermittent Catheterization. Spinal Cord. Jul. 2009;47(7):565-569.

Proctor et al., Small colony variants: a pathogenic form of bacteria that facilitates persistent and recurrent infections. Nat Rev Microbiol. Apr. 2006;4(4):295-305.

Reid et al., Potential uses of probiotics in clinical practice. Clin Microbiol Rev. Oct. 2003;16(4):658-72.

Trautner et al., Pre-inoculation of urinary catheters with *Escherichia coli* 83972 inhibits catheter colonization by Enterococcus faecalis. J Urol. Jan. 2002;167(1):375-9.

International Search Report and Written Opinion for PCT/US2015/023026, dated Aug. 21, 2015, 15 pages.

U.S. Appl. No. 11/137,948, filed May 26, 2005.

EZ Rich Defined Medium, *E. coli* Genome Project, University of Wisconsin-Madison, www.genome.wisc.edu/resources/protocols/ezmedium.htm, retrieved Jan. 31, 2019, 5 pages.

\* cited by examiner

PREPARATION OF SMALL COLONY VARIANTS OF THERAPEUTIC BACTERIA

The present application claims priority to U.S. Provisional Application Ser. No. 61/971,913, filed Mar. 28, 2014, which is incorporated herein by reference.

FIELD OF THE INVENTION

The present invention relates to methods of preparing and using small colony variants of probiotic organisms, e.g., non-pathogenic strains of E. coli.

BACKGROUND OF THE INVENTION

Bacteriuria and pyuria are uniformly present in patients who have indwelling urinary catheters. Antimicrobial therapy may transiently eradicate the bacteria, but bacteriuria promptly recurs, and the infecting bacteria become progressively resistant to antibiotics. Antimicrobial (e.g., antibiotic and/or antiseptic) treatment of asymptomatic urinary tract infections (UTI) in catheterized patients has not been shown to be of benefit, as treated and untreated catheterized patients have a similar prevalence of infection a few weeks after the end of treatment, and an equal likelihood of developing symptomatic episodes of UTI (Nicolle, L. E., Drugs Aging 22(8): 627-39 (2005). Additionally, antimicrobial treatment of asymptomatic catheter-associated UTIs (CAUTIs) has been associated with the emergence of drug-resistant organisms, complicating management when symptomatic infections occur.

Studies have indicated that pre-colonization of the bladder with certain non-pathogenic strains of E. coli is a safe and effective way of preventing or reducing the in vivo incidence of urinary catheter colonization by a wide variety of uropathogens.

SUMMARY OF THE INVENTION

The present invention relates to the preparation and propagation of particular variant forms of non-pathogenic E. coli. In some embodiments, small colony variants selected for use in therapeutic preparations, e.g., in freeze-dried preparations of lubricant gels containing probiotic microbes. The invention relates to methods of differentiation, isolation, propagation, and storage of small colony variants (SCVs) of E. coli, preferably E. coli 83972 or E. coli HU2117, or modified or variant forms thereof, and methods for using the prepared bacteria to establish biofilms in treated subjects.

In some embodiments, the technology provides methods of culturing SCVs of probiotic bacteria, preferably in liquid culture. In some embodiments, the methods comprise isolating an E. coli small colony variant (SCV) bacterium, inoculating a liquid growth medium with the SCV bacterium, wherein the liquid growth medium is a supplemented minimal medium comprising a a source of carbon such as a sugar or sugar alcohol, and further comprising the amino acids cysteine, methionine, serine, and lysine. Preferably, the liquid growth medium does not comprise added adenine, cytosine, guanine, uracil, yeast extract, or an enzymatic digest of complex protein. In some embodiments, the liquid culture medium comprises a buffered solution, such as a 3-(N-morpholino)propanesulfonic acid (MOPS) buffer solution. In certain preferred embodiments the MOPS solution comprises a MOPS/tricene solution.

Methods of culturing SCV bacteria further comprise incubating an inoculated liquid growth medium under conditions in which the SCV bacterial strain grows to produce a liquid culture of bacterial cells that maintain the SCV form, with minimal reversion to the normal or "large colony variant" (LCV) form. In some embodiments, the liquid culture of SCV bacterial cells comprises fewer than 50%, preferably fewer than 40%, preferably fewer than 30%, preferably fewer than 20%, preferably fewer than 10%, preferably fewer than 5%, preferably fewer than 1%, more preferably fewer than 0.1% of corresponding normal or LCV form of the bacteria. In some preferred embodiments, the liquid culture of SCV bacterial cells is free or essentially free of corresponding LCV bacterial cells.

In some embodiments, the source of carbon comprises glycerol, and in certain preferred embodiments, the source of carbon consists essentially of glycerol, in that glycerol is the sole added carbon source in the liquid growth medium.

In some embodiments, isolating the SCV form of E. coli comprises isolating an SCV bacterium from urine. In some embodiments, the urine is biological, i.e., it is urine produced by a human or animal, while in some embodiments, the urine is synthetic or artificial urine. In some embodiments, the SCV bacterium is cultured in urine. Culturing SCV bacteria in urine may occur in a body (in vivo, e.g., in the urinary tract of an individual) or it may occur outside a body (ex vivo, e.g., in a vessel in a laboratory).

In some embodiments, isolating an SCV bacterium comprises growing the SCV bacterium on a solid culture medium, e.g., on an agar-containing medium such as Mac-Conkey's agar or LB agar.

In some embodiments, the liquid growth medium, e.g., a supplemented minimal medium as discussed above, further comprises one or more amino acids selected from asparagine, aspartic acid, glycine, phenylalanine, and tryptophan. The liquid culture medium may also contain one or more salts. In some embodiments, the liquid growth medium comprises one or more of ferrous sulfate, ammonium chloride, potassium sulfate, calcium chloride, magnesium chloride, and sodium chloride, and in some embodiments, the liquid growth medium further comprises one or more of ammonium molybdate, boric acid, cobalt chloride, cupric sulfate, manganese chloride and zinc sulfate.

In certain embodiments, the liquid growth medium is a defined medium that consists essentially of:

| | |
|---|---|
| MOPS | 40 mM |
| 3-(N-Morpholino)-propanesulfonic acid | 4 mM |
| Tricine | |
| Iron Sulfate | 10 µM |
| Ammonium Chloride | 9.5 mM |
| Potassium Sulfate | 276 µM |
| Calcium Chloride Monohydrate | 0.5 µM |
| Magnesium Chloride | 525 µM |
| Sodium Chloride | 50 mM |
| Ammonium Molybdate | $2.92 \times 10^{-9}$ M |
| Boric Acid | $4 \times 10^{-7}$ M |
| Cobalt Chloride | $3.02 \times 10^{-8}$ M |
| Cupric Sulfate | $9.62 \times 10^{-9}$ M |
| Manganese Chloride | $8.08 \times 10^{-8}$ M |
| Zinc Sulfate | $9.74 \times 10^{-9}$ M |
| Potassium Phosphate, Dibasic | 1.32 mM |
| Alanine | 0.798 mM |
| Arginine HCl | 5.2 mM |
| Asparagine | 0.4 mM |
| Aspartic Acid, Potassium Salt | 0.4 mM |
| Cysteine Monohydrate HCl | 0.1 mM |
| Glutamic Acid, Potassium Salt | 0.7 mM |
| Glutamine | 0.6 mM |
| Glycine | 0.8 mM |
| Histidine monohydrate HCl | 0.2 mM |

| | |
|---|---|
| Isoleucine | 0.4 mM |
| Leucine | 0.8 mM |
| Lysine DiHydrochloride | 0.4 mM |
| Methionine | 0.2 mM |
| Phenylalanine | 0.4 mM |
| Proline | 0.4 mM |
| Serine | 10.0 mM |
| Threonine | 0.4 mM |
| Tryptophane | 0.1 mM |
| Tyrosine | 0.2 mM |
| Valine | 0.6 mM |
| Thiamine HCl | 0.01 mM |
| Calcium Pantothenate | 0.01 mM |
| ρ-aminobenzoic acid | 0.01 mM |
| ρ-hydroxybenzoic acid | 0.01 mM |
| 2,3-dihydroxybenzoic acid | 0.01 mM |
| Glycerol | 0.4% (w/v) |
| Water | |

In some embodiments, the technology provides viable probiotic SCV *E. coli* bacteria in a medical lubricant gel, e.g., for lubricating a medical device prior to use. In preferred embodiments, use of the probiotic gel composition induces formation of a biofilm of said *E. coli* bacteria, e.g., on the surface of a treated medical device/and or on a tissue surface exposed to the treated device, such as in the urinary tract of a patient.

In some embodiments, providing a lubricant gel containing SCV *E. coli* bacteria comprises the steps of a) providing in an aqueous fluid a mixture comprising i) a liquid culture of probiotic SCV bacterial cells, as described above, ii) a pharmaceutically acceptable gelling agent, and iii) a pharmaceutically acceptable protective agent; and b) freezing the mixture to produce a frozen preparation of bacteria mixed with lubricant gel. In some embodiments, the frozen preparation is then dried under vacuum to produce a freeze-dried preparation, e.g., for stable storage.

Freeze-dried preparations of probiotic *E. coli* bacteria and lubricant gels may be prepared as described, e.g., in U.S. patent application Ser. No. 12/671,370, which is incorporated herein by reference in its entirety. The gelling agent is selected to provide a suitable lubricant function during use, when the preparation is either thawed (if frozen) or reconstituted with liquid (if freeze-dried). In some embodiments, the gelling agent comprises one or more of hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, or poloxamer. In certain preferred embodiments, the gelling agent comprises or consists of hydroxyethyl cellulose.

In some embodiments, the aqueous fluid mixture containing the SCV bacteria further comprises a pharmaceutically acceptable second protective agent that is different from the first protective agent. In certain embodiments, the first and second protective agents comprise one or more of non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and/or an amino acid hydrochloride.

In some embodiments, the technology provides a frozen or a freeze-dried composition comprising probiotic *E. coli* SCV bacterial cells, produced according to the methods described above. In some embodiments, the preparation of SCV bacterial cells comprises fewer than 50%, preferably fewer than 40%, preferably fewer than 30%, preferably fewer than 20%, preferably fewer than 10%, preferably fewer than 5%, preferably fewer than 1%, more preferably fewer than 0.1% of corresponding normal or LCV forms of the bacteria. In some preferred embodiments, the preparation of SCV bacterial cells is free or essentially free of corresponding LCV bacterial cells.

In some embodiments, the technology provides a method of forming a biofilm on a medical device by treating the device with a preparation of SCV *E. coli* bacterial cells. In some embodiments, the technology comprises a) providing a freeze-dried preparation comprising SCV bacterial cells, a pharmaceutically acceptable gelling agent, and a pharmaceutically acceptable protective agent; b) exposing the freeze dried preparation to an aqueous fluid to form a medically acceptable lubricant gel comprising an effective amount of the SCV bacterial cells; c) contacting the medical device with the lubricant gel to produce a treated device; and d) exposing the treated device to conditions in which a biofilm of the bacterial cells forms on the treated device and/or on a tissue exposed to the treated device.

In some embodiments, the method of forming a biofilm on a medical device comprises a) providing a frozen preparation comprising a preparation of SCV bacterial cells, e.g., as described above, a pharmaceutically acceptable gelling agent, and a pharmaceutically acceptable protective agent; b) thawing the frozen preparation to form a medically acceptable lubricant gel comprising an effective amount of the SCV bacterial cells; c) contacting the medical device with the lubricant gel to produce a treated device; and d) exposing the treated device to conditions wherein a biofilm forms from the SCV bacterial cells on the treated device and/or on a tissue exposed to the treated device.

In some embodiments, the medical device is a urinary catheter. In certain embodiments, the exposing of the treated device to biofilm-forming conditions comprises contacting a subject, e.g., a patient, with the treated device.

In additional embodiments, the technology provides methods of administering SCV bacterial cells to a subject, comprising a) providing a freeze-dried preparation comprising a mixture of preparation of SCV bacterial cells, a pharmaceutically acceptable gelling agent, and a pharmaceutically acceptable protective agent; b) exposing the freeze dried preparation to an aqueous fluid to form a medically acceptable lubricant gel comprising an effective amount of the SCV bacterial cells; and c) contacting the subject with the lubricant gel. In other embodiments, the technology provides methods of administering SCV bacterial cells to a subject, comprising a) providing a frozen preparation comprising a mixture of a preparation of SCV bacterial cells, a pharmaceutically acceptable gelling agent, and a pharmaceutically acceptable protective agent; b) thawing the frozen preparation to form a medically acceptable lubricant gel comprising an effective amount of the SCV bacterial cells; and c) contacting a subject with the lubricant gel.

In certain embodiments, contacting a subject with the gel comprises contacting a medical device with the lubricant gel to produce a treated device, and contacting the subject with the treated device. In certain preferred embodiments, the medical device is a urinary catheter.

The technology further provides kits for convenient use of the compositions and methods described above. For example, in some embodiments, the technology is provided as a kit comprising, e.g., i) a freeze-dried or frozen composition mixture comprising SCV *E. coli* bacterial cells, as described above. In certain embodiments in which the composition is provided in freeze-dried form, the kit may further comprise a container of sterile aqueous fluid, e.g., water, for re-suspending the freeze-dried mixture to produce a lubricant gel containing an effective amount of the SCV bacteria. In some embodiments, the kit further comprises a medical device, e.g., a catheter such as a urinary catheter.

DESCRIPTION OF THE DRAWING

FIGS. 1A-1C show the colony morphology of large and small colony variants of *E. coli* HU2117 on MacConkey agar (A), LB agar (B), or modified MOPS minimal agar (C). Large-colony variants are streaked on the left of each plate, and small-colony variants are streaked on the right.

FIG. 2 shows MacConkey agar plates streaked with two different glycerol freezer stocks of SCV-form *E. coli* HU2117. The left plate shows HU2117 Stock A; the right plate shows HU2117 Stock B.

FIG. 3 shows LB agar plates streaked with two different glycerol freezer stocks of SCV-form *E. coli* HU2117. The left plate shows HU2117 Stock A; the right plate shows HU2117 Stock B.

FIG. 4 show MacConkey agar plates streaked with two different glycerol freezer stocks of LCV-form *E. coli* 83972. The left plate shows 83972 Stock A; the right plate shows 83972 Stock B.

FIG. 5 show LB agar plates streaked with two different glycerol freezer stocks of LCV-form *E. coli* 83972. The left plate shows 83972 Stock A; the right plate shows 83972 Stock B.

FIG. 6 shows MacConkey agar plates streaked with glycerol freezer stocks of SCV and LCV forms of *E. coli* 83972. The left plate shows SCV-form CON42-5; the right plate shows LCV-form CON19-4A.

FIG. 7 shows LB agar plates streaked with glycerol freezer stocks of SCV and LCV forms of *E. coli* 83972. The left plate shows SCV-form CON42-5; the right plate shows LCV-form CON19-4A.

FIGS. 8A and 8B show MacConkey and LB agar plates streaked with glycerol stocks of SCV forms of *E. coli* 83972 and HU2117 prepared as described herein. The left plates of 8A and 8B show 83972 and the right plates show HU2117.

DEFINITIONS

To facilitate an understanding of the present invention, a number of terms and phrases are defined below:

Small colony variant (SCV) refers to a variant of *E. coli* characterized in that, when grown on solid media, it forms colonies that are substantially smaller than the normal colony size of the corresponding parent strain. For example, SCVs of *E. coli* typically form colonies that, after overnight incubation, are pinpoint in size on the agars on which they grow, while the LCVs form colonies of normal size, e.g., 1 mm or larger in diameter, when well separated from other colonies. See, for example, FIG. 1, which compares LCVs and SCVs of *E. coli* HU2117 on MacConkey's agar, Luria-Bertani (LB) agar, and on a modified MOPS minimal agar. SCV colonies of an *E. coli* strain generally measure one tenth or less the diameter of the normal or large colony variants of the same organism. While colonies are generally not formed during cultivation in liquid medium, the form of the microbe is deemed to be "SCV" if, when the liquid culture is streaked on solid culture media and incubated to form colonies, the resulting colonies are predominantly or exclusively in the SCV form.

Large colony variant as used herein refers to the variant having normal size, generally being at least 10-fold larger in diameter than SCVs of the same organism when grown identically.

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a probiotic microbe, and optionally one or more other agents) for a condition characterized by the presence of pathogenic bacteria, or in anticipation of possible exposure to pathogenic bacteria.

The term "diagnosed," as used herein, refers to the recognition of a disease (e.g., caused by the presence of pathogenic bacteria) by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reactions that occur within a natural environment.

As used herein, the term "virulence" refers to the degree of pathogenicity of a microorganism, e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

As used herein, the term "effective amount" refers to the amount of a composition (e.g., a probiotic microbe) sufficient to effect beneficial or desired results. An effective amount can be administered in one or more administrations, applications or dosages and is not intended to be limited to a particular formulation or administration route. It is within the skilled artisan's ability to relatively easily determine an effective amount of a probiotic microbe or other therapeutic composition.

As used herein, the term "administration" refers to the act of giving a drug, prodrug, or other agent, or therapeutic treatment (e.g., compositions of the present invention) to a physiological system (e.g., a subject or in vivo, in vitro, or ex vivo cells, tissues, and organs). Exemplary routes of administration to the human body can be through the urethra, eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "treating a surface" refers to the act of exposing a surface, e.g., of a catheter, to one or more compositions of the present invention. Methods of treating a surface include, but are not limited to, spraying, misting, submerging, and coating.

As used herein, the term "co-administration" refers to the administration of at least two agent(s) (e.g., two separate donor bacteria, each comprising a different plasmid) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell (including, e.g., a bacterial cell prepared according to the methods herein), or a tissue as compared to the same cell or tissue prior to the administration of the toxicant.

As used herein, the term "pharmaceutical composition" refers to the combination of an active agent (e.g., a probiotic microbe) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., epithelial, alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject contacted by a pathogenic microorganism or that prevent infectivity, morbidity, or onset of mortality in a host contacted by a pathogenic microorganism. As used herein, therapeutic agents encompass agents used prophylactically, e.g., in the absence of a pathogen, in view of possible future exposure to a pathogen. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

As used herein, the terms "probiotic" and "probiotic microbe" are used interchangeably to refer to a live microorganism that is administered in adequate amounts to confer a health benefit on the host. See, e.g., *Potential Uses of Probiotics in Clinical Practice*, G. Reid, et al., Clinical Microbiology Reviews, October 2003, p 658-672, incorporated herein by reference. Probiotics are not limited to microorganisms administered by any particular route. Exemplary routes of administration to the human body can be through the eyes (ophthalmic), mouth (oral), skin (transdermal), nose (nasal), lungs (inhalant), oral mucosa (buccal), vagina, rectum, urethra, ear, by injection (e.g., intravenously, subcutaneously, intratumorally, intraperitoneally, etc.) and the like. As used herein, the term "probiotic" includes but is not limited to naturally occurring organisms and derivatives thereof, e.g., *E. coli* 83972, and *E. coli* HU2117. Probiotic organisms may also be modified, e.g., through selective culturing or recombinant engineering, to have altered properties. For example, probiotic microbes configured to contain conjugatively transmissible plasmids that alter recipient cells (e.g., to kill or to reduce pathogenicity of a pathogen recipient cell) also find use with the present invention. See, e.g., U.S. application Ser. Nos. 11/137,950 and 11/137,948, each of which is incorporated herein by reference in its entirety.

As used herein, the term "microbe" refers to a microorganism and is intended to encompass both an individual organism, or a preparation comprising any number of the organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

The term "non-pathogenic bacteria" or "non-pathogenic bacterium" includes all known and unknown non-pathogenic bacterium (Gram-positive or Gram-negative) and any pathogenic bacterium that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

As used herein, the term "liquid culture" refers to a preparation of an organism that has been grown in a liquid culture medium, e.g., LB broth, MOPS minimal medium, such that the resulting liquid contains a distribution of the organisms, e.g., bacteria.

A "liquid culture medium" may be of any liquid composition suitable to provide nutrients to the organism to be grown. A solidifying agent, e.g., agar, may be added to produce a "solid culture medium", e.g., culture plates or slants, also referred to as agar plates and agar slants.

As used herein, the terms "inoculate" and "inoculation" as verbs refer to the act of introducing an organism into an environment free of that organism, e.g., using a sample or colony of *E. coli* to inoculate a sterile culture medium in order to cultivate the strain of *E. coli*.

As used herein, the term "incubate" refers to holding an item or sample (e.g., an inoculated culture, a chemical or enzymatic reaction mixture) at a temperature for a period of time or until a particular result (e.g., orgasm growth or reaction result) occurs.

As used herein, the term "urine" refers to a liquid preparation having the essential elements found in biological urine, i.e., urine produced by a human or animal. Urine may be natural or synthetic. For example, a synthetic urine preparation may comprise a mixture of Peptone 137 yeast extract, lactic acid, citric acid, sodium bicarbonate, urea uric acid, creatinine, calcium chloride, sodium chloride, iron II sulfate, magnesium sulfate, sodium sulfate, potassium dihydrogen phosphate, di-potassium hydrogen phosphate, and ammonium chloride, each at an physiological concentration in water. See, e.g., Brooks and Keevil, Letters in Applied Microbiology 1997, (24):203-206, "A simple artificial urine for the growth of urinary pathogens", and Souhaila Bouatra, et al., PLOSOne, September 2013; Volume 8/Issue 9/e73076, each of which is incorporated herein by reference in its entirety.

As used herein, the term "biofilm" refers to a cohesive matrix of organisms, e.g., *E. coli* bacteria, adhered to a surface. A biofilm typically comprises an extracellular polymeric substance (comprising, e.g., polysaccharides) exuded by the organism(s), which is a matrix in which the cells are embedded and which adheres the cells to each other and to the surface. A surface supporting a biofilm may be a non-biological surface (e.g., the surface of a medical device) or may be biological (e.g., a tissue surface in a subject). Biofilms may comprise multiple species or may be formed by a single species of microbe.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "kit" refers to any delivery system for delivering materials. In the context of reaction materials such as probiotic microbes, such delivery systems include but are not limited to systems that allow for the storage, transport, or delivery of appropriate reagents (e.g., cells, buffers, culture media, selection reagents, etc., in the appropriate containers) and/or devices (e.g., catheters, syringes, reaction tubes or plates, culture tubes or plates) and/or supporting materials (e.g., media, written instructions for performing using the materials, etc.) from one location to another. For example, kits include one or more enclosures (e.g., boxes, bags) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain a dried composition of a microbe with a gelling agent for a particular use, while a second container contains sterile fluid such as water or buffer for dissolving or resuspending a dried composition. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

With regards to the dried cake produced by lyophilization of a composition, the term "elegant" is used in the literature to describe a 'perfect' lyophilization product with no cracks, no shrinkage, with smooth edges, and a fluffy consistency.

As used herein, the terms "a" and "an" means at least one, and may refer to more than one.

The term "bacterial interference" as used herein refers to an antagonistic interaction between bacteria and other microorganisms to establish themselves and dominate their environment. Bacterial interference operates through several mechanisms, e.g., production of antagonistic substances, changes in the bacterial microenvironment, competition for attachment sites, and reduction of needed nutritional substances.

The term "coating" as used herein refers to a layer of material covering, e.g., a medical device or a portion thereof. A coating can be applied to the surface or impregnated within the material of the implant.

As used herein, the term "antimicrobial agent" refers to a composition other than a probiotic that decreases, prevents or inhibits the growth of bacterial and/or fungal organisms. Examples of antimicrobial agents include, e.g., antibiotics and antiseptics.

The term "antiseptic" as used herein is defined as an antimicrobial substance that inhibits the action of microorganisms, including but not limited to alpha.-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic effect. Some examples of combinations of antiseptics include a mixture of chlorhexidine, chlorhexidine and chloroxylenol, chlorhexidine and methylisothiazolone, chlorhexidine and (.alpha.-terpineol, methylisothiazolone and alpha.-terpineol; thymol and chloroxylenol; chlorhexidine and cetylpyridinium chloride; or chlorhexidine, methylisothiazolone and thymol. These combinations provide a broad spectrum of activity against a wide variety of organisms.

As used herein, the term "dried" as used in reference to a probiotic composition refers to removing the solvent component or components to levels that no longer support chemical reactions. The term is also used in reference to a composition that has been dried (e.g., a dried preparation or dried composition). Those of skill in the art will appreciate that a composition may be "dried" while still having residual solvent or moisture content after lyophilization, or that a dried composition may, after the end of the drying process, absorb moisture hygroscopically, e.g., from the atmosphere. The term "dried" encompasses a composition with increased moisture content due to hygroscopic absorption.

As used herein, the term "protective agent" refers to a composition or compound that protects the activity or integrity of an active agent (e.g., an enzyme, a probiotic microbe) when the active agent is exposed to certain conditions (e.g., drying, freezing). In some embodiments, a protective agent protects a living organism (e.g., a probiotic microbe) during a freezing process (i.e., it is a "cryoprotectant"). Examples of protective agents include but are not limited to non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

As used herein, the term "gelling agent" refers to a composition that, when dissolved, suspended or dispersed in a fluid (e.g., an aqueous fluid such as water or a buffer solution), forms a gelatinous semi-solid (e.g., a lubricant gel). Examples of gelling agents include but are not limited to hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

As used herein, the term "excipient" refers to an inactive ingredient (i.e., not pharmaceutically active) added to a preparation of an active ingredient. The gelling and protective agents described herein are referred to generally as "excipients."

As used herein, the term "consists essentially of" as used in reference to a composition means that the composition consists of the recited component(s), and that the composition includes no other components that would materially change the characteristics of the recited composition (e.g., does not contain other active ingredients). For example, traces of an impurity, or de minimus amounts of one or more additional components that do not change the characteristics of the composition would fall within the scope of the recited composition. Similarly, as used in reference to a method or series of steps, the term refers to a method of set of steps that is limited to the recited steps, admitting only de minimus deviation that would not materially change the characteristics of the steps or results of the recited method.

DETAILED DESCRIPTION OF THE INVENTION

The present invention is directed to methods and materials useful for treating surfaces with non-pathogenic organisms, e.g., bacteria. In particular embodiments, the methods and materials find use in establishing a bacterial culture on a subject, e.g., on the surfaces of the urinary tract of a subject, and/or on a surface of a medical device, e.g., a urinary catheter. In particular embodiments, the culture comprises a biofilm. Embodiments of the invention are directed to therapeutic preparations of small colony variant (SCV) forms of bacteria, e.g., E. coli, for use in establishing a culture and/or a biofilm in the urinary tract of a subject.

Embodiments of the invention are described in this Description, and in the Summary of the Invention, above, which is incorporated here by reference. Although the invention has been described in connection with specific embodiments, it should be understood that the invention as claimed should not be unduly limited to such specific embodiments. For example, discussions herein pertaining to E. coli 83972 also encompass E. coli HU2117, as HU2117 is a version of 83972 engineered to have a deletion in the papG gene. The growth characteristics of these strains have been observed to be the same.

Small colony variants (SCVs) are a naturally occurring subpopulation of bacteria that forms colonies on solid media that are markedly smaller than the colonies formed by the parental bacteria. SCVs, e.g., of E. coli, may be about one tenth of the diameter of the normal or "large colony variant" (LCV) form of the same strain grown on the same solid medium. See, e.g., Proctor, et al., Nature Rev. Micro., 4:295-305 (2006). During development of the technology, it has been observed that SCV forms of E. coli 83972 and E. coli HU2117 are particularly useful in establishing therapeutic biofilms, e.g., on catheter surfaces and/or in the urinary tract of a treated subject.

Isolates of non-pathogenic E. coli 83972 and/or E. coli HU2117 from subjects having asymptomatic urinary tract infections show a mixture of small and large colony forms of these strains. As discussed in more detail below, the small and large colony variants can be readily distinguished by looking at colony morphology on agar plates, with MacConkey's agar being particularly revealing of the size difference.

During development of the present technology, it was determined that standard rich media typically used for broth culture of bacteria (e.g., Luria Bertani (LB) or other media supplemented with a complete source of amino acids, such as with yeast extract, tryptone, peptone, etc.) promotes reversion from the SCV form to the LCV form in E. coli 83972 and E. coli HU2117.

In addition, the SCV forms of these E. coli strains are auxotrophic for numerous amino acids, while the LCV forms of the same strains are not. Thus, the SCV strains require supplemented media for growth and minimal media can be used to select against their growth. For example, the SCVs of E. coli 83972 and E. coli HU2117 have absolute requirements for the amino acids cysteine, methionine, serine, and lysine, and less essential requirements for asparagine, aspartic acid, glycine, phenylalanine, and tryptophan. In contrast, the LCV forms are not auxotrophs and may readily be grown in MOPS minimal medium supplemented with a carbon source (e.g., 0.2% of either glucose or glycerol). Thus, it can be seen that it is relatively simple to find growth conditions to reduce the occurrence of SCVs, and difficult to find growth conditions that select for growth of the SCV forms and against the LCV forms. This makes it difficult to produce liquid cultures in which the population of cells is predominantly in SCV form, and still more difficult to produce liquid cultures that are essentially completely SCV-form bacteria.

The present invention relates to the development of methods for isolation, growth, and storage of SCVs of E. coli strains, particularly non-pathogenic strains E. coli 83972, E. coli HU2117, and variants thereof or derived therefrom.

The present invention is directed to methods and compositions for the production of cultures that are predominantly SCV, preferably completely SCV, such that any LCV-form E. coli in the liquid culture are reduced in number or are non-existent. Thus, an aspect of the invention is the identification of growth conditions that identify and maintain the SCV form of E. coli strains, e.g., E. coli 83972 and E. coli HU2117, for use in manufacturing probiotic preparations, e.g., for coating catheters. In preferred embodiments, the bacteria are grown in liquid culture without the use of antimicrobial components, e.g., copper (Hirsch, J Bacteriol. 81:448-58 (1961); 2-methyl-1,4-naphthoquinone (see, e.g., Colwell, J Bacteriol. 52(4):417-22 (1946).

An aspect of the present invention is selection of an SCV form of E. coli for therapeutic use, e.g., to create biofilms. It has been determined that using the SCV form of probiotic E. coli in the compositions and methods of the technology described herein is effective in producing a biofilm of the probiotic strains in the urinary tract of the treated subject and/or on the surface of a urinary catheter. The technology thus provides methods of differentiation, isolation, propagation, and storage of small colony variants (SCVs) of E. coli, preferably E. coli 83972 or E. coli HU2117, or modified or variant forms thereof, and methods for using the prepared bacteria to establish biofilms in treated subjects.

The technology further provides methods and compositions for delivering an effective amount of probiotic SCV E. coli to a subject or patient. While not limiting the present invention to any particular formulation or mode of administration, in some preferred embodiments, the probiotic microbe is present in prepared lubricant gel mixture in a concentration of about $10^7$ to cfu $10^9$ per ml of lubricant gel.

Growth Characteristics of E. coli Strains 83972 and HU2117

During development of the technology and cultivation of the E. coli strains discussed herein, E. coli strains 83972 and HU2117, observation of small and large colony variant growth characteristics of these strains indicated the following:

1. Streaking a mixed culture comprising SCV and LCV forms of the strain on MacConkey's agar showed the two colony morphologies clearly and distinctly, such that fresh SCV colonies could be selected for further steps. The difference in morphology, although apparent on LB agar, is less clear on this medium.

2. Extended culture of E. coli HU2117 in rich media (e.g., LB or tryptic soy) results in a shift of the culture from small to large colony morphology. While small colony variant populations can give rise to cells having the large colony phenotype under several culture conditions tested, it is difficult to shift the phenotype of a particular LCV isolate to produce a population of SCV microbes.

3. Passage of SCVs isolates on MacConkey's agar maintains the small colony phenotype over time.

4. Small colony variants did not grow on MOPS minimal medium or in MOPS minimal broth.

5. MOPS minimal medium inoculated with an SCV inoculum will after several days, become turbid, predominantly by the growth of cells having LCV morphology, indicating that the development of turbidity occurs either because of conversion of cells from small- to large-colony morphology, and/or from the survival and replication of a minority population of LCVs in the SCV inoculum. This indicates that using only minimal medium for culture of these strains would favor cultivation of LCV forms of *E. coli* HU2117 and 83972.

6. During development of the technology, it was determined that use of glycerol as the carbon source (in place of glucose, for example) reduces the rate of reversion to LCV form, and thereby helps to maintain the SCV morphology during liquid culturing.

EXPERIMENTAL

The following examples are provided in order to demonstrate and further illustrate certain preferred embodiments and aspects of the present invention and are not to be construed as limiting the scope thereof.

In the experimental disclosure that follows, the following abbreviations apply: ° C. (degrees Celsius); cm (centimeters); g (grams); l or L (liters); ml or mL (milliliters); μl or μL (microliters); μg (micrograms); μm (micrometers); μM (micromolar); μmol (micromoles); mg (milligrams); mm (millimeters); mM (millimolar); mmol (millimoles); M (molar); mol (moles); ng (nanograms); nm (nanometers); nmol (nanomoles); N (normal); pmol (picomoles); bp (base pairs); cfu (colony forming units).

EXAMPLE 1

Defining Conditions for Culturing Small Colony Variant Forms of *E. coli* 83972 and HU2117

The initial characterization of *E. coli* 83972 and HU2117 started by trying to define a good synthetic growth medium for the culture of these *E. coli* strains. Strain HU2117 is an engineered variant of 83972 having an engineered deletion in the papG gene.

Several different media (both agar plates and broths) were tried to find an acceptable media that could be used for manufacturing, and that could also aid in distinguishing between the small and large colony variants. Two commercially available mediums, EZ Rich Defined medium and MOPS minimal medium, were purchased from Teknova (Hollister, Calif.). Two different carbon sources, glucose and glycerol, were used in combination with these two different media. The strains were also streaked and maintained on different agars, including MacConkey's, TSA and LB agars. The media and agars were formulated as shown below:

| MOPS Defined Medium (e.g., EZ Rich Defined Medium) | | |
|---|---|---|
| Component # | Description | Amount |
| 1 | 10X MOPS Mixture | 100 mL |
| 2 | 0.132M K$_2$HP04 | 10 mL |
| 3 | 10X ACGU | 100 mL |
| 4 | 5X Supplement EZ | 200 mL |
|  | Sterile H$_2$O* | 580 mL |
|  | 20% Glucose or Glycerol | 10 mL |
|  | Total | 1000 mL |

| MOPS Minimal Medium | | |
|---|---|---|
| Component # | Description | Amount |
| 1 | 10X MOPS Mixture (see below) | 100 mL |
| 2 | 0.132M K$_2$HP04 | 10 mL |
|  | Sterile H$_2$O* | 880 mL |
|  | 20% Glucose or Glycerol | 10 mL |
|  | Total | 1000 mL |

| MOPS Media Components | | |
|---|---|---|
| #1 MOPS Modified Rich Buffer | 10X Concentration | 1X Concentration |
| MOPS (MW 209.3) | 400 mM | 40 mM |
| Tricine (MW 179.2) | 40 mM | 4.0 mM |
| Iron Sulfate Stock | 0.1 mM | 0.01 mM |
| Ammonium Chloride | 95 mM | 9.5 mM |
| Potassium Sulfate | 2.76 mM | 0.276 mM |
| Calcium Chloride | 0.005 mM | 0.0005 mM |
| Magnesium Chloride | 5.25 mM | 0.525 mM |
| Sodium Chloride | 500 mM | 50 mM |
| Ammonium Molybdate | $3 \times 10^{-8}$ M | $3 \times 10^{-9}$ M |
| Boric Acid | $4 \times 10^{-6}$ M | $4 \times 10^{-7}$ M |
| Cobalt Chloride | $3 \times 10^{-7}$ M | $3 \times 10^{-8}$ M |
| Cupric Sulfate | $10^{-7}$ M | $10^{-8}$ M |
| Manganese Chloride | $8 \times 10^{-7}$ M | $8 \times 10^{-8}$ M |
| Zinc Sulfate | $10^{-7}$ M | $10^{-8}$ M |
| #2 Potassium Phosphate Dibasic Solution | 100X Concentration | 1X Concentration |
| Potassium Phosphate Dibasic | 132 mM | 1.32 mM |
| #3 ACGU Solution | 10X concentration | 1X concentration |
| Potassium Hydroxide | 15 mM | 1.5 mM |
| Adenine | 2.0 mM | 0.2 mM |
| Cytosine | 2.0 mM | 0.2 mM |
| Uracil | 2.0 mM | 0.2 mM |
| Guanine | 2.0 mM | 0.2 mM |
| #4 5X Supplement | 5X concentration | 1X concentration |
| L-Alanine | 4.0 mM | 0.8 mM |
| L-Arginine | 26 mM | 5.2 mM |
| L-Asparigine | 2.0 mM | 0.4 mM |
| L-Aspartic Acid, Potassium Salt | 2.0 mM | 0.4 mM |
| L-Glutamic Acid, Potassium Salt | 3.3 mM | 0.66 mM |
| L-Glutamine | 3.0 mM | 0.6 mM |
| L-Glycine | 4.0 mM | 0.8 mM |
| L-Histidine HCl H2O | 1.0 mM | 0.2 mM |
| L-Isoleucine | 2.0 mM | 0.4 mM |
| L-Proline | 2.0 mM | 0.4 mM |
| L-Serine | 50 mM | 10 mM |
| L-Threonine | 2.0 mM | 0.4 mM |

| MOPS Media Components | | |
|---|---|---|
| L-Tryptophan | 0.5 mM | 0.1 mM |
| L-Valine | 3.0 mM | 0.6 mM |
| L-Leucine | 4.0 mM | 0.8 mM |
| L-Lysine | 2.0 mM | 0.4 mM |
| L-Methionine | 1.0 mM | 0.2 mM |
| L-Phenylalinine | 2.0 mM | 0.4 mM |
| L-Cysteine HCl | 0.5 mM | 0.1 mM |
| L-Tyrosine | 1.0 mM | 0.2 mM |
| Thiamine | 0.05 mM | 0.01 mM |
| Calcium Pantothenate | 0.05 mM | 0.01 mM |
| para-Amino Benzoic Acid | 0.05 mM | 0.01 mM |
| para-Hydroxy benzoic Acid | 0.05 mM | 0.01 mM |
| di Hydroxy Benzoic Acid | 0.05 mM | 0.01 mM |

| | 10X concentration | 1X concentration |
|---|---|---|
| 20% Glucose Solution | | |
| Glucose | 20% | 2.00% |
| 20% Glycerol Solution | | |
| Glycerol | 20% | 2.00% |

(See, e.g., Teknova; F. C. Neidhardt, P. L. Bloch, and D. F. Smith. 1974. Culture medium for enterobacteria. J Bacteriol 119(3): 736-747)

MacConkey's Agar:
 Peptone (Difco) or Gelysate (BBL) 17.0 g
 Proteose peptone (Difco) or Polypeptone (BBL) 3.0 g
 Lactose 10.0 g
 NaCl 5.0 g
 Crystal Violet 1.0 mg
 Neutral Red 30.0 mg
 Bile Salts 1.5 g
 Agar 13.5 g
 Distilled Water Add to make 1 Liter
 pH adjusted to 7.1+/−0.2

Tryptic Soy Agar:
 Casein peptone (pancreatic) 15.0 g
 Soya peptone (papainic) 5.0 g
 Sodium chloride 5.0 g
 Agar 15.0 g
 Distilled water added to make 1 Liter
 pH adjusted to 7.3+/−0.2.

Luria-Bertani Broth and Agar:
 Tryptone 10 g
 Yeast Extract 5 g
 NaCl 10 g
 Agar 15.0 g
 Distilled water added to make 1 Liter Broth forms of the media above omit the agar component. All are sterilized, e.g., by autoclaving at 15 psi, from 121-124° C. for about 15 minutes.

i. Comparison of Small and Large Colony Variants of *E. coli* HU2117 on Three Agars During the course of developing the technology, it was observed that the SCV forms of these *E. coli* strains will not grow in modified MOPS minimal broth or agar, formulated as described above. The appearances of large and small colony variants on MacConkey's agar, LB agar, and modified MOPS minimal agar are shown in FIG. 1. The left side of each plate was streaked with LCV form, and the right side of each plate was streaked with SCV form. All plates were incubated for the same period of time. While the colony size difference can be observed on the LB plate (FIG. 1B), the streaks are similar enough in appearance that the SCV form could be overlooked. In contrast, on the MacConkey's plate (FIG. 1A), the SCV colonies have grow to a small fraction of the size of the LCV colonies. The MOPs minimal media plate clearly shows that the SCV form do not grow on this medium.

ii. Small-to-Large Colony Conversion Rate in Rich Media

Using glycerol stocks of strains having exclusively SCVs, it was possible to calculate small-to-large colony conversion rates in different types of liquid media.

EZ Rich Defined Glycerol Medium

SCV stocks were used to inoculate a broth of EZ Rich defined glycerol medium (described above). After incubation, aliquots of the cultures were diluted and plated onto LB agar (to show all colonies) and onto MOPS minimal glucose agar plates (on which SCVs cannot grow) so that the relative amounts of each morphological type in the culture could be determined. Only two colonies grew on the MOPS minimal glucose plates, showing that the broth culture (and the original stock) to be nearly completely composed of SCV isolates.

Calculating the total number of large colonies that would be in this culture (accounting for dilutions) and the total number of *E. coli* HU2117 in the culture, the per bacterium conversion rate in glycerol-based medium was determined to be $1.4 \times 10^{-9}$.

EZ Rich Defined Glucose Medium

Similar stocks were used to inoculate EZ Rich defined glucose medium. After incubation, aliquots of the cultures were diluted and plated onto LB agar and onto MOPS minimal glucose agar plates, so that the relative amounts of each morphological type in the liquid culture could be determined. Thirty three colonies grew on the MOPS minimal glucose plates, showing a per bacterium conversion rate in the glucose-based medium of $3.04 \times 10^{-8}$.

These data show that using glycerol as a sole carbon source for in liquid cultures produces a slower rate of conversion, and that glycerol is preferred over glucose for maintenance of the SCV morphology.

In a specific embodiment, the liquid culture medium for preparing SCV forms of *E. coli*, e.g., strains 83972 and HU2117 have the following formulation (prior to inoculation):

TABLE 1

| | |
|---|---|
| MOPS 3-(N-Morpholino)-propanesulfonic acid | 40 mM |
| Tricine | 4 mM |
| Iron Sulfate | 10 µM |
| Ammonium Chloride | 9.5 mM |
| Potassium Sulfate | 276 µM |
| Calcium Chloride Monohydrate | 0.5 µM |
| Magnesium Chloride | 525 µM |
| Sodium Chloride | 50 mM |
| Ammonium Molybdate | $2.92 \times 10^{-9}$ M |
| Boric Acid | $4 \times 10^{-7}$ M |
| Cobalt Chloride | $3.02 \times 10^{-8}$ M |
| Cupric Sulfate | $9.62 \times 10^{-9}$ M |
| Manganese Chloride | $8.08 \times 10^{-8}$ M |
| Zinc Sulfate | $9.74 \times 10^{-9}$ M |
| Potassium Phosphate, Dibasic | 1.32 mM |
| Alanine | 0.798 mM |
| Arginine HCl | 5.2 mM |
| Asparagine | 0.4 mM |

TABLE 1-continued

| | |
|---|---|
| Aspartic Acid, Potassium Salt | 0.4 mM |
| Cysteine Monohydrate HCl | 0.1 mM |
| Glutamic Acid, Potassium Salt | 0.7 mM |
| Glutamine | 0.6 mM |
| Glycine | 0.8 mM |
| Histidine monohydrate HCl | 0.2 mM |
| Isoleucine | 0.4 mM |
| Leucine | 0.8 mM |
| Lysine DiHydrochloride | 0.4 mM |
| Methionine | 0.2 mM |
| Phenylalanine | 0.4 mM |
| Proline | 0.4 mM |
| Serine | 10.0 mM |
| Threonine | 0.4 mM |
| Tryptophane | 0.1 mM |
| Tyrosine | 0.2 mM |
| Valine | 0.6 mM |
| Thiamine HCl | 0.01 mM |
| Calcium Pantothenate | 0.01 mM |
| p-aminobenzoic acid | 0.01 mM |
| p-hydroxybenzoic acid | 0.01 mM |
| 2,3-dihydroxybenzoic acid | 0.01 mM |
| Glycerol | 0.4% (w/v) |
| Water | | iii. Stored Isolates of SCVs Maintain SCV Conformation

Two different glycerol stocks of the SCV form of *E. coli* HU2117 (stocks A and B, see FIGS. 2 and 3) and two different stocks of the LCV form of *E. coli* 83972 (stocks A and B, see FIGS. 4 and 5) were used to streak both LB agar and MacConkey agar plates.

Figure 2:
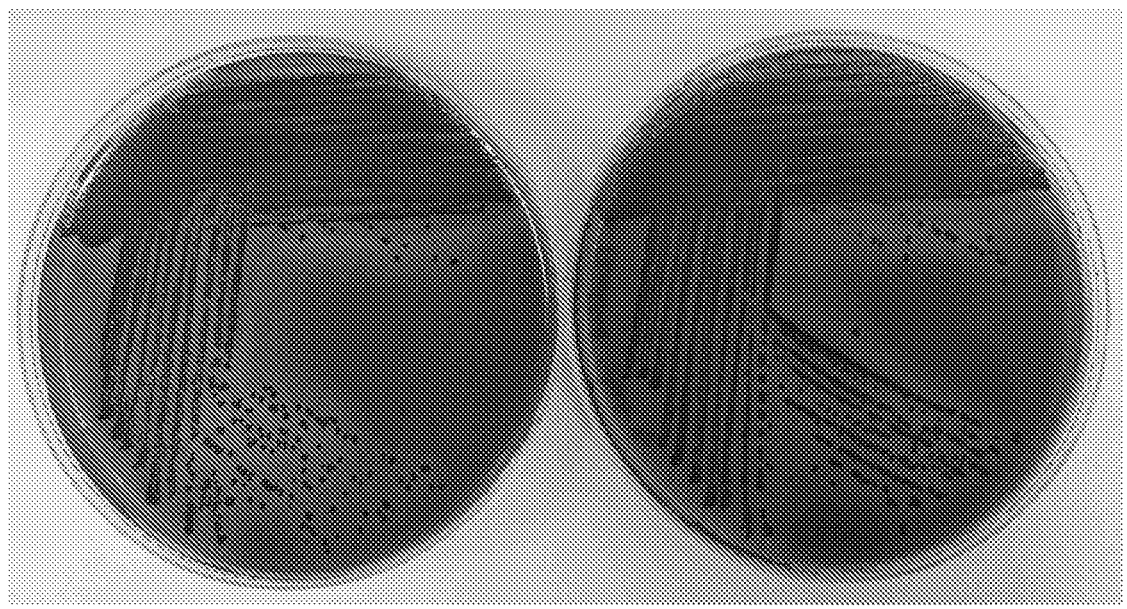
Figure 3:
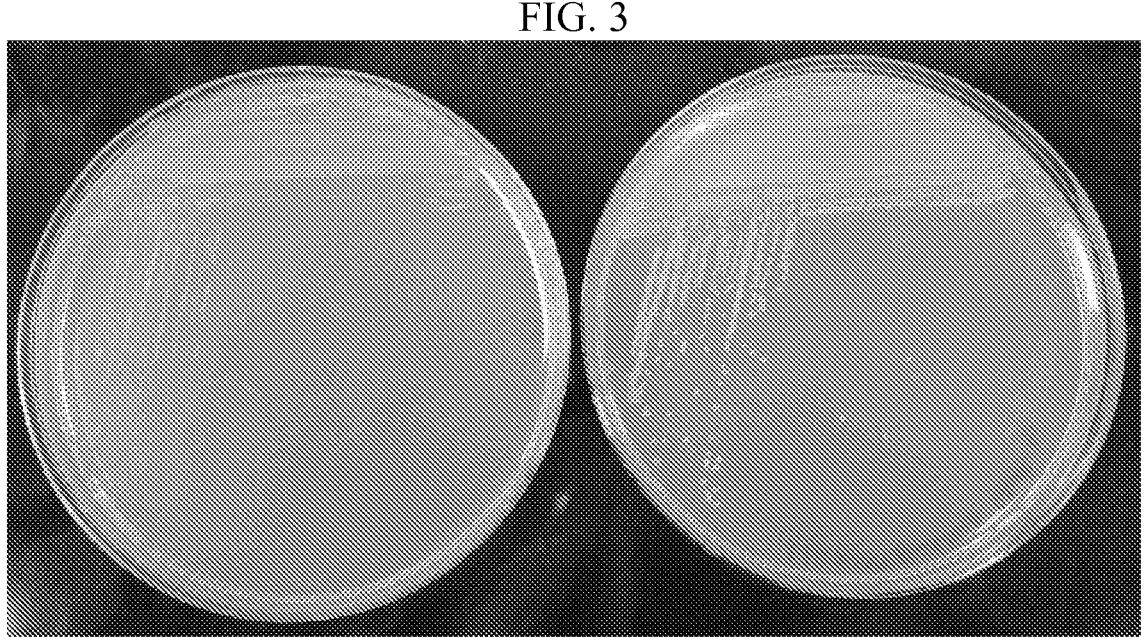
Figure 4:
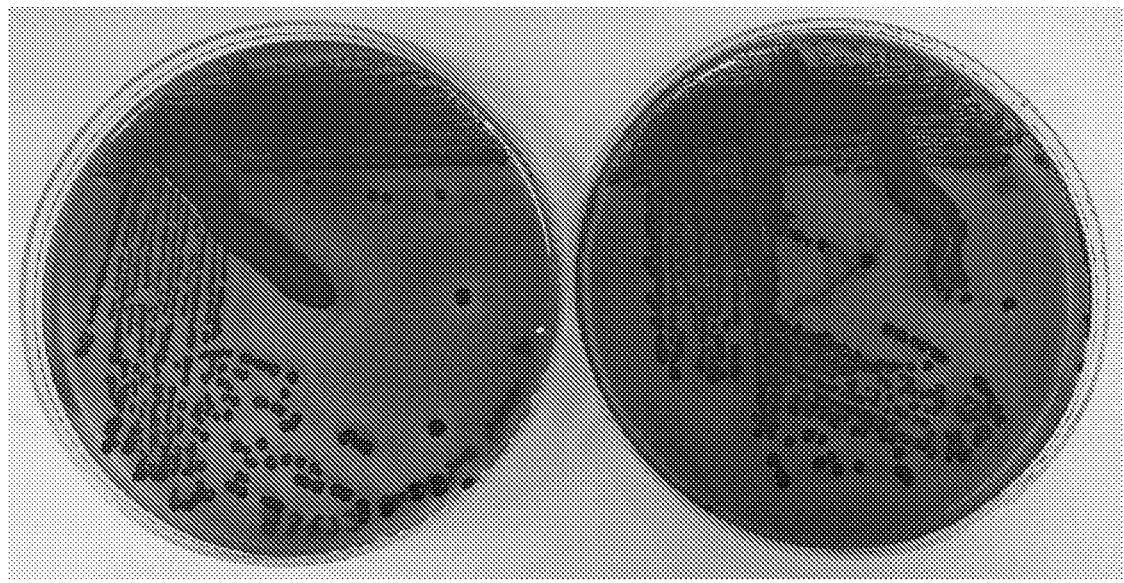

After 24 hours of incubation at 37° C., good growth was observed on all plates that were streaked. FIG. 2 and FIG. 3, show resulting MacConkey agar plates and LB agar plates that were streaked with *E. coli* HU2117. All colonies on both the MacConkey agar plates (FIG. 2) and on the LB plates (FIG. 3) showed a small colony morphology.

Figure 5:
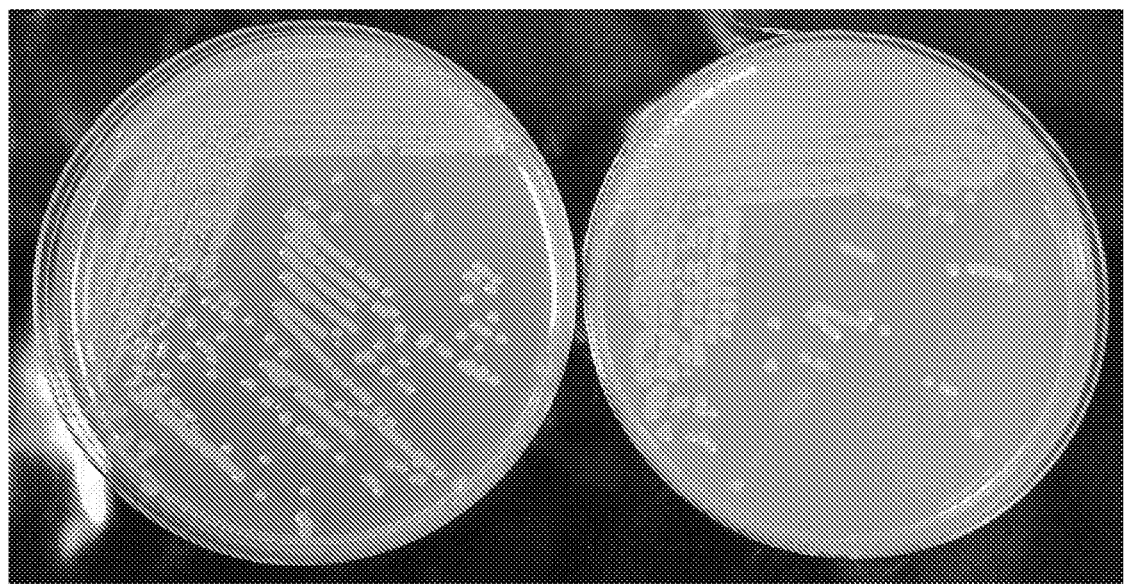

The plates streaked with the stocks of *E. coli* 83972 almost uniformly showed the LCV derivative. Both stocks A and B of *E. coli* 83972 looked identical when these were streaked out onto either MacConkey agar (FIG. 4) or LB agar (FIG. 5). It is noted that these plates were left in the 37° C. for the same amount of time as the HU2117 streaked plates shown in FIGS. 2 and 3, which demonstrates that the difference in colony size is not a result of different incubation times.

To prepare additional stocks of SCV cells, e.g., *E. coli* HU2117 SCV cells, for storage, e.g., at −80° C., approximately 50 colonies are inoculated into a 1-liter flask and containing 125 mL of the modified EZ rich defined medium described in Table 1, above. The cells are grown for 16 hours, and all the culture in the flask is harvested by centrifugation. The pellet is resuspended in about 11 mL of modified EZ rich defined medium. When the cells are resuspended, 11 mL of 2× freezing medium (the same modified EZ rich defined medium containing 50% glycerol) is added and the cells are placed on ice. The cell suspension is chilled on ice for 60 minutes before aliquoting into vials, e.g., at a volume of 1.0 mL/vial ($3.6 \times 10^9$ cfu/mL). After the cells are aliquoted into vials, they are frozen and stored at −80° C. Preferably, vials that are removed from −80° C. storage are used only once.

iv. Comparison of Small and Large Colony Variants of *E. coli* 83972

One MacConkey agar plate and one LB agar plate were streaked with each of an SCV-form of *E. coli* 83972 ("CON42-5") and an LCV-form of *E. coli* 83972 ("CON19-4A"). The plates were incubated for 24 hours at 37° C., and are shown in FIGS. 6 and 7.

Figure 6:
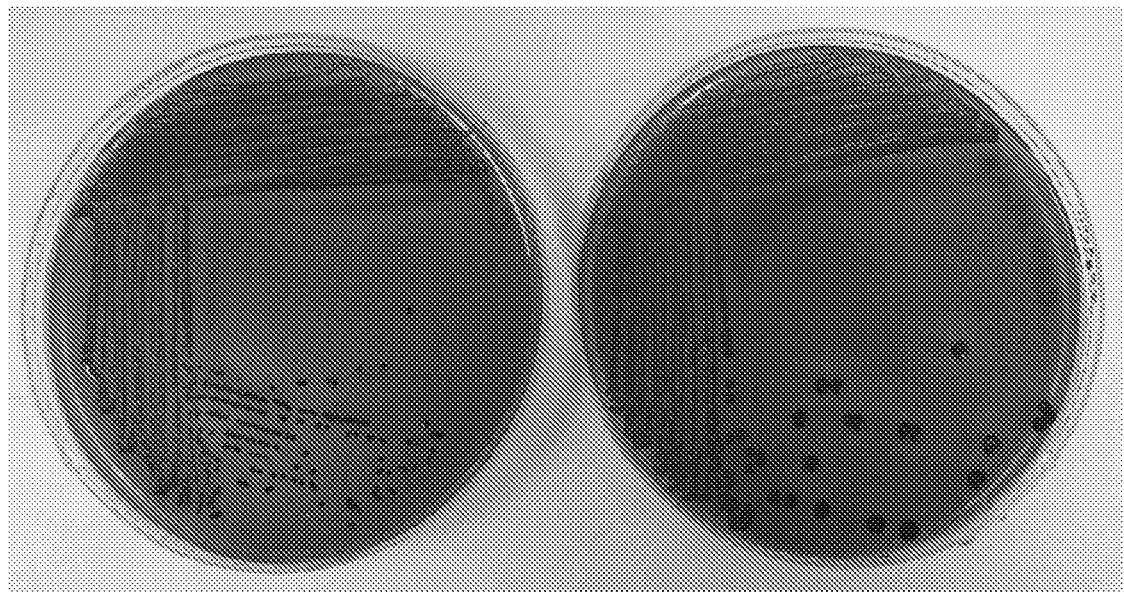
Figure 7:
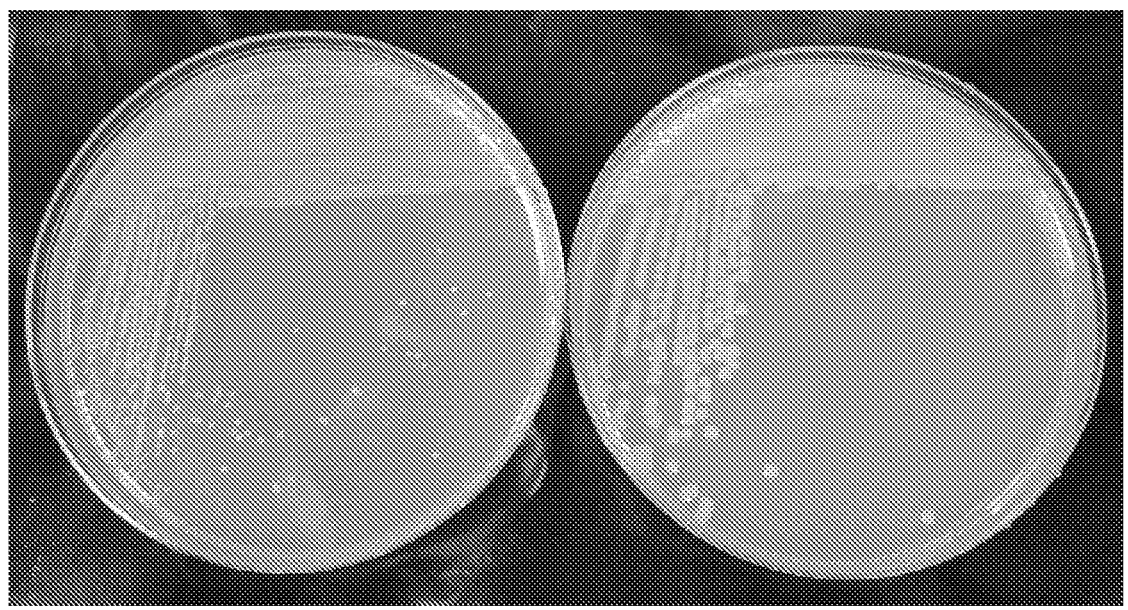
Figure 8A:
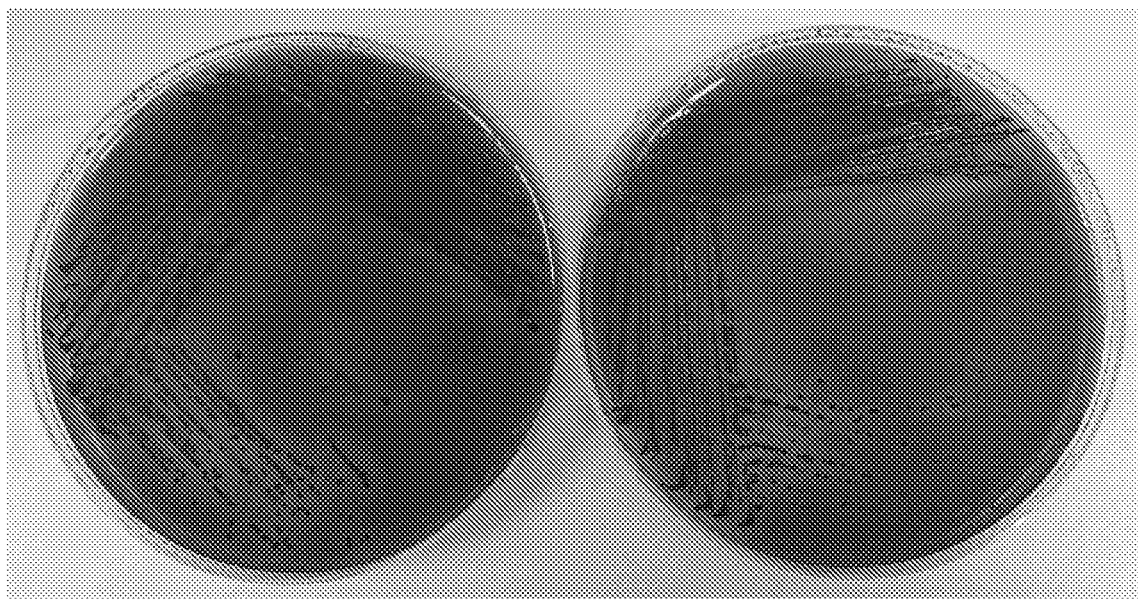
Figure 8B:
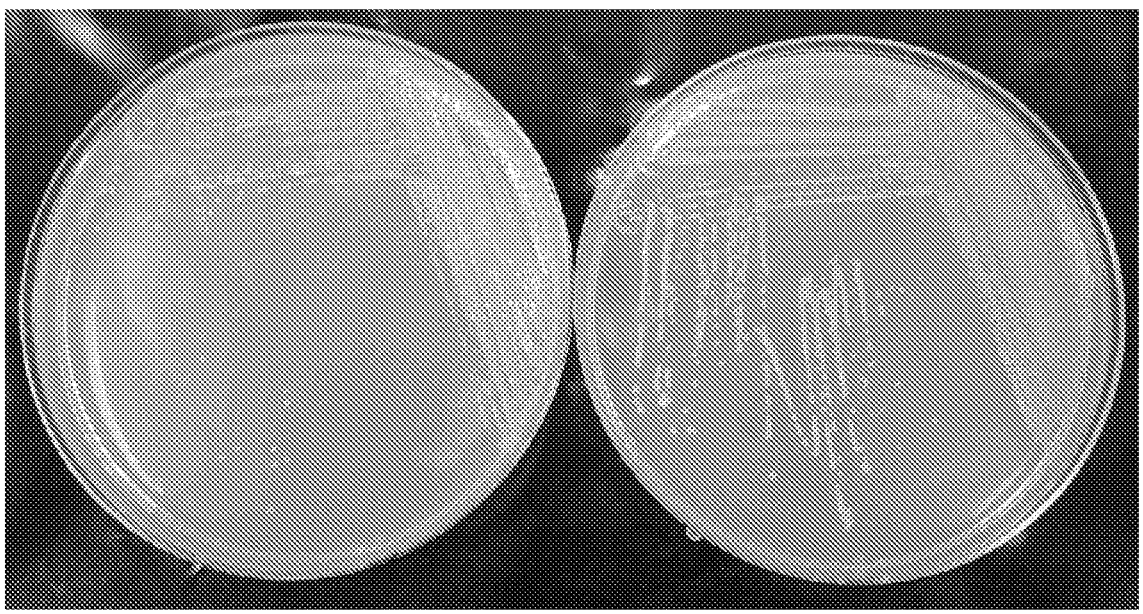

The colony size variants on the MacConkey agar plates shown in FIG. 6 are readily distinguishable from each other. The plate streaked with CON42-5 (on the left) shows the small colony morphology, largely pinpoint colonies, and the plates streaked with the LCV-form CON19-4A isolate (on the right) clearly show large colony morphology. The same colony morphologies are observed on the LB agar plates streaked with the same glycerol freezer stocks (FIG. 7).

v. Confirmation That Small and Large Colony Variants are the Same Strain

SCV and LCV forms of *E. coli* HU2117, having the different growth requirements discussed above, were characterized to verify that they were genetically identical. To isolate large-colony variants, *E. coli* HU2117 was streaked directly onto modified MOPS minimal medium, which only supports the growth of large-colony variants, and on MacConkey agar, which supports the growth of both large- and small-colony variants. After 40 hours of growth at 37° C., several large colonies were obtained on the MOPS minimal agar plates. Both large- and small-colony variants were streaked onto MacConkey agar, then restreaked onto MacConkey agar and Luria-Bertani (LB) agars, and incubated at 37° C. for 18 hours. Representative comparisons showing large- and small-colony variants on both MacConkey agar and LB agar are shown in FIG. 1. Analysis of both colony variants shows the serotype of both variants to be O6:H1, which is the same for both strain HU2117 and the wild-type strain 83972.

vi. Confirmation of Strain Identity

The identity is further confirmed by PCR amplification. Both 83972 and HU2117 possess a 1.6 kb cryptic plasmid that is unique to these strains, the presence of which distinguishes these strains from other *E. coli* strains. In addition, the papG gene of HU2117 has an engineered 803 bp deletion that easily distinguishes HU2117 from its parental strain 83972, and from other *E. coli* strains that possess the pap operon. PCR using primer pairs specific for cryptic plasmid and for the papG deletion confirms that both SCV and LCV isolates are *E. coli* HU2117.

By way of example, Table 2 describes a panel of tests that may be used to verify the identity of HU2117 strain:

TABLE 2

| Tests for: | Method | Specification (Result) |
|---|---|---|
| papG minus genotype | PCR and sequencing | PCR amplification of a strain-specific 1584 bp fragment. The flanking region of the deleted papG should not show any unexpected alteration compared to that of *E. coli* 83972 |
| Genetic verification of species | Phylogenetic analysis of 16S rRNA sequence | Phylogenetically closest to *Escherichia coli* |
| Biochemical verification of species | β-glucuronidase activity | Blue-color colony on Chromocult TBX agar medium (EMD Biosciences) |
| Plasmid ID | PCR | Amplification of three fragments specific to the plasmid |
| RFLP | PFGE | Unique patterns of RFLP specific to *E. coli* HU2117, distinguishable from other *E. coli* strains |
| Antibiotic susceptibility | Growth in the presence of antibiotics | Susceptible to all antibiotics tested |

EXAMPLE 2

Preparation of a Freeze-Dried Lubricant Gel Containing SCV-Form E. coli HU2117

This example provides an exemplary method of producing a freeze-dried lubricant gel containing an effective amount of SCV-form of E. coli HU2117. Additional freeze-dried preparations and methods of making and using them are described, e.g., in U.S. Patent Publication 2009/0041727, published Feb. 12, 2009, which is incorporated herein in its entirety, for all purposes.

By way of example and not by way of limitation, the starting quantity is selected so as to maintain an effective level of viability in cells freeze-dried in a composition comprising a gelling agent. For example, in some embodiments, a preferred concentration of viable SCV cells might be approximately $10^8$ cfu/ml. If a vial (or other container) of the preparation is to be suspended or dissolved, e.g., in 10 ml of water, the dried cake in the vial would optimally have approximately $10^9$ viable cells.

Cell Preparation

One 2 liter flask of cells is grown from 1 ml of SCV HU2117 seed stock inoculated into 1 L Modified EZ Rich Defined Glycerol medium, incubated at 37±1° C. for 8 hrs with constant shaking at 250 RPM, or to an $OD_{600}$ of about 2-2.3.

The cells are collected by centrifugation, e.g., at 4° C., at 6000 RPM for 8 min. The pelleted cells are washed, e.g., twice with 0.9% saline and once with 10 mM citrate buffer, pH 7.0.

The pelleted cells are resuspended into 2-3 ml of buffer, e.g., of 10 mM citrate buffer, pH 7.0, for a final volume of approximately 10 ml.

The concentration of the resuspended cells may be determined using plate counts.

Lyophilization 0.5 ml of resuspended cells are mixed with 1.5 ml of an excipient, e.g, 5 to 10% sucrose, and a sterile lubricant gel, e.g., 10 ml of 2% autoclaved hydroxyethyl cellulose (HEC).

The mixture is lyophilized, e.g., as described below"

| Process step | Step description |
| --- | --- |
| Loading | Incubate at 5° C. and one atmosphere for 60 min |
| Freezing | Ramp shelf to −45° C. at an average controlled rate of 5° C./min. Control shelf at target set point of −45° C. for 285 min. |
| Primary drying/ Secondary drying | Evacuate chamber, control at a target set point of 60 mTorr.<br>(a) Ramp shelf to −30° C. at an average controlled rate of 0.2° C./min. Control shelf at target set point of −30° C. for 2850 min.<br>(b) Ramp shelf to −22° C. at an average controlled rate of 0.2° C./min. Control shelf at target set point of −22° C. for 1080 min.<br>(c) Ramp shelf to −10° C. at an average controlled rate of 0.2° C./min. Control shelf at target set point of −10° C. for 600 min.<br>(d) Control chamber pressure at a target set point of 60 mTorr. Ramp shelf to 25° C. at controlled average rate of 0.2° C./min Control shelf at target set point for 720 min |

After drying, the dried cake may be resuspended, e.g., in about 10 to 12 ml of distilled water, for testing to determine bacterial viability and/or for use as a lubricant gel, e.g., to coat a catheter prior to insertion, wherein the catheter is lubricated and the subject into whom the catheter is inserted are inoculated in a manner conducive to formation of a biofilm of E. coli HU2117 in the urinary tract and/or on the inserted catheter.

Using the growth conditions described herein above, the proportion of large colonies in a final product can be maintained at an extremely low level (e.g., frequency of 1 in $1.0 \times 10^8$ cfu/ml).

All publications and patents mentioned in the above specification are herein incorporated by reference for all purposes. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of culturing probiotic bacteria, comprising:
   a) isolating an E. coli small colony variant (SCV) bacterium to form a preparation of SCV E. coli bacterial cells that is free of large colony variant (LCV) E. coli bacterial cells, wherein said E. coli SCV bacterium is selected from E. coli 83972 and E. coli HU2117, or a variant or derivative thereof;
   b) inoculating a liquid growth medium with said preparation of SCV E. coli bacterial cells, wherein said liquid growth medium is a supplemented minimal medium comprising:
      i) a buffer solution;
      ii) a sugar or sugar alcohol; and
      iii) cysteine, methionine, serine, and lysine,
      wherein said liquid growth medium does not comprise added adenine, cytosine, guanine, uracil, yeast extract, or an enzymatic digest of complex protein;
   c) incubating said liquid growth medium inoculated with said preparation of SCV E. coli bacterial cells to produce a liquid culture of SCV E. coli bacterial cells, wherein fewer than 50% of E. coli bacterial cells in the liquid culture are LCV E. coli bacterial cells.

2. The method of claim 1, wherein said sugar or sugar alcohol comprises glycerol.

3. The method of claim 2, wherein said sugar or sugar alcohol consists of glycerol as the sole added carbon source in said liquid growth medium.

4. The method of claim 1, wherein in said liquid culture of SCV E. coli bacterial cells, fewer than 30% of E. coli bacterial cells in the liquid culture are LCV E. coli bacterial cells.

5. The method of claim 1, wherein said liquid culture of SCV E. coli bacterial cells is free of LCV E. coli bacterial cells.

6. The method of claim 1 wherein said isolating comprises isolating an SCV bacterium from urine.

7. The method of claim 1, wherein said isolating comprises growing an SCV bacterium in urine, wherein said urine comprises one or more of natural urine and synthetic urine.

8. The method of claim 1, wherein said isolating comprises growing said SCV bacterium on a solid culture medium.

9. The method of claim 8, wherein said solid culture medium is MacConkey's agar.

10. The method of claim 1, wherein said buffer solution is a 3-(N-morpholino)propanesulfonic acid (MOPS) buffer solution.

11. The method of claim 10, wherein said MOPS buffer is MOPS/tricine.

12. The method of claim 1, wherein said liquid growth medium further comprises one or more amino acids selected from asparagine, aspartic acid, glycine, phenylalanine, and tryptophan.

13. The method of claim 1, wherein said liquid growth medium comprises one or more of ferrous sulfate, ammonium chloride, potassium sulfate, calcium chloride, magnesium chloride, and sodium chloride.

14. The method of claim 1, wherein said liquid growth medium further comprises one or more of ammonium molybdate, boric acid, cobalt chloride, cupric sulfate, manganese chloride and zinc sulfate.

15. The method of claim 1, wherein said liquid growth medium consists essentially of:

| | |
|---|---|
| MOPS | 40 mM |
| (3-(N-morpholino)- propanesulfonic acid) | 4 mM |
| Tricine | |
| Iron Sulfate | 10 µM |
| Ammonium Chloride | 9.5 mM |
| Potassium Sulfate | 276 µM |
| Calcium Chloride Monohydrate | 0.5 µM |
| Magnesium Chloride | 525 µM |
| Sodium Chloride | 50 mM |
| Ammonium Molybdate | $2.92 \times 10^{-9}$ M |
| Boric Acid | $4 \times 10^{-7}$ M |
| Cobalt Chloride | $3.02 \times 10^{-8}$ M |
| Cupric Sulfate | $9.62 \times 10^{-9}$ M |
| Manganese Chloride | $8.08 \times 10^{-8}$ M |
| Zinc Sulfate | $9.74 \times 10^{-9}$ M |
| Potassium Phosphate, Dibasic | 1.32 mM |
| Alanine | 0.798 mM |
| Arginine HCl | 5.2 mM |
| Asparagine | 0.4 mM |
| Aspartic Acid, Potassium Salt | 0.4 mM |
| Cysteine Monohydrate HCl | 0.1 mM |
| Glutamic Acid, Potassium Salt | 0.7 mM |
| Glutamine | 0.6 mM |
| Glycine | 0.8 mM |
| Histidine monohydrate HCl | 0.2 mM |
| Isoleucine | 0.4 mM |
| Leucine | 0.8 mM |
| Lysine DiHydrochloride | 0.4 mM |
| Methionine | 0.2 mM |
| Phenylalanine | 0.4 mM |
| Proline | 0.4 mM |
| Serine | 10.0 mM |
| Threonine | 0.4 mM |
| Tryptophane | 0.1 mM |
| Tyrosine | 0.2 mM |
| Valine | 0.6 mM |
| Thiamine HCl | 0.01 mM |
| Calcium Pantothenate | 0.01 mM |
| ρ-aminobenzoic acid | 0.01 mM |
| ρ-hydroxybenzoic acid | 0.01 mM |
| 2,3-dihydroxybenzoic acid | 0.01 mM |
| Glycerol | 0.4% (w/v) |
| Water | |

* * * * *